United States Patent
Palmer et al.

(10) Patent No.: US 10,905,136 B2
(45) Date of Patent: Feb. 2, 2021

(54) HIGH THROUGHPUT PROCESS FOR DELIVERING SEMI-FIRM GEL FOR POULTRY

(71) Applicant: ClearH2O, Inc., Westbrook, ME (US)

(72) Inventors: Jay Palmer, Brunswick, ME (US); Paul Dioli, Yarmouth, ME (US)

(73) Assignee: CLEAR H2O, INC., Westbrook, ME (US)

( * ) Notice: Subject to any disclaimer, the term of this patent is extended or adjusted under 35 U.S.C. 154(b) by 514 days.

(21) Appl. No.: 15/328,582

(22) PCT Filed: Aug. 11, 2016

(86) PCT No.: PCT/US2016/046443
§ 371 (c)(1),
(2) Date: Jan. 24, 2017

(87) PCT Pub. No.: WO2017/030876
PCT Pub. Date: Feb. 23, 2017

(65) Prior Publication Data
US 2017/0208839 A1 Jul. 27, 2017

Related U.S. Application Data

(60) Provisional application No. 62/205,324, filed on Aug. 14, 2015, provisional application No. 62/222,345, filed on Sep. 23, 2015.

(51) Int. Cl.
| | | |
|---|---|---|
| *A61D 7/00* | (2006.01) | |
| *A23K 50/75* | (2016.01) | |
| *A61K 9/06* | (2006.01) | |
| *A61K 9/08* | (2006.01) | |
| *A23K 20/163* | (2016.01) | |
| *A01K 13/00* | (2006.01) | |
| *A01K 45/00* | (2006.01) | |
| *A61K 47/36* | (2006.01) | |
| *A23K 40/00* | (2016.01) | |
| *A01K 39/00* | (2006.01) | |

(52) U.S. Cl.
CPC ............ *A23K 50/75* (2016.05); *A01K 13/003* (2013.01); *A01K 39/00* (2013.01); *A01K 45/00* (2013.01); *A23K 20/163* (2016.05); *A23K 40/00* (2016.05); *A61D 7/00* (2013.01); *A61K 9/06* (2013.01); *A61K 9/08* (2013.01); *A61K 47/36* (2013.01)

(58) Field of Classification Search
CPC .................. A01K 13/001; A01K 39/01; A01K 45/00–45/007; A23K 50/70; A23K 50/75; A61D 1/025; A61D 7/00; A61D 11/00
USPC .............................. 119/72.5, 665; 424/271.1
See application file for complete search history.

(56) References Cited

U.S. PATENT DOCUMENTS

| | | |
|---|---|---|
| 883,132 A | 3/1908 | Goff |
| 3,148,649 A | 9/1964 | Moore |
| 3,559,621 A | 2/1971 | Willauer, Jr. |
| 3,875,763 A | 4/1975 | Synder |
| 3,876,763 A | 4/1975 | Yoshikazu |
| 4,316,464 A | 2/1982 | Peterson |
| 4,752,475 A | 6/1988 | Davis |
| 5,474,102 A | 12/1995 | Lopez |
| 5,478,557 A | 12/1995 | Nisbet |
| 6,910,446 B2 | 6/2005 | Johnston Jr. |
| 8,794,185 B2 | 8/2014 | Lee |
| 9,157,054 B2 | 10/2015 | Bhandari |
| 10,155,034 B2 | 12/2018 | Lee |
| 10,279,024 B2 | 5/2019 | Lee |
| 2002/0104485 A1 | 8/2002 | Lewis et al. |
| 2002/0173545 A1 | 11/2002 | Gutzmann |
| 2008/0190373 A1* | 8/2008 | Lee .................. A01K 45/00 119/72 |
| 2010/0137451 A1 | 6/2010 | Demarco et al. |
| 2011/0008293 A1* | 1/2011 | Bhandari ............... A01N 25/28 424/93.6 |
| 2013/0004601 A1* | 1/2013 | Nielsen ................. A23L 29/231 424/734 |
| 2013/0156827 A1* | 6/2013 | Li ....................... A61K 31/4709 424/400 |
| 2014/0255366 A1* | 9/2014 | Yde ......................... C12N 1/04 424/93.45 |

FOREIGN PATENT DOCUMENTS

| | | |
|---|---|---|
| CA | 2169987 | 8/1996 |
| CA | 2416726 A1 | 7/2004 |
| CA | 2427907 A1 | 7/2004 |
| CA | 2464522 A1 | 10/2005 |
| EP | 0600723 A2 | 6/1994 |
| EP | 3334289 B1 | 10/2019 |
| JP | 2009207963 A | 9/2009 |
| JP | 2012105564 A | 6/2012 |
| JP | 2013169207 A | 9/2013 |
| WO | 96/25951 A1 | 8/1996 |
| WO | 9908704 A1 | 2/1999 |
| WO | 2005/099617 A1 | 10/2005 |
| WO | 2009062254 A1 | 5/2009 |
| WO | 2011011873 A1 | 2/2011 |

OTHER PUBLICATIONS

Imeson, Thickening and Gelling Agents for Food, Springer Science+Business Media Dordrecht, p. 22-44. (Year: 1997).*

(Continued)

*Primary Examiner* — Walter A Moore
(74) *Attorney, Agent, or Firm* — Hayes Soloway

(57) ABSTRACT

A high throughput process for delivering a semi-firm gel for supplying vaccines, nutritive substances and other similar material to animals, such as poultry chicks. The material is delivered in a non-absorbent semi-firm gel that is easily consumable which results in higher material uptake. The semi-firm gel is formed by interactions occurring between a solution containing an alginic acid crosslinking agent with a gel containing alginic acid.

11 Claims, No Drawings

(56) References Cited

OTHER PUBLICATIONS

Kariduraganavar et al., Polymer Synthesis and Processing, Natural and Synthetic Biomedical Polymers, 2014 Elsevier Inc., p. 1-31. (Year: 2014).*

Gombotz W R et al: "Protein release from alginate matrices". Advanced Drug Delivery Reviews. Elsevier. Amsterdam. NL vol. 31. No. 3, May 4, 1998 (May 4, 1998)

* cited by examiner

HIGH THROUGHPUT PROCESS FOR DELIVERING SEMI-FIRM GEL FOR POULTRY

BACKGROUND INFORMATION

Field of the Invention

The invention relates to a high throughput process of delivering non-smearing, semi-firm gel to poultry chicks.

Discussion of the Prior Art

The use of gels and water spray to deliver hydration, vaccination, medication, and nutrition to poultry chicks is known in the industry. The common process is as follows: 1) a large number of chicks are placed in a box that is sent down a conveyor line; 2) along the line, the box of chicks passes under a series of spray cabinets where the chicks are sprayed with vaccines and other substances that are dispersed in water and/or gel; and 3) once fully vaccinated, the box is removed from the conveyor and delivered to a farm or poultry-raising facility. The vaccines and other substances that are dispersed in the water and/or gel are delivered as a coarse spray or small gel droplets which the chicks consume off of one another by preening. It is common for the chicks to be sprayed with a number of separate solutions as they travel along the conveyor. This process is a high throughput process, typically taking 1 second or less to spray the box of chicks. Up to 500,000 chicks can be processed daily.

Conventional gels are soft, lack durability and often smear when applied to chicks. As the chicks are repeatedly sprayed, their downs become wet and some of the vaccine or deliverable substance is absorbed into the down or dissipates to the point where it cannot be consumed. The gel continues to smear to the point where it is difficult or impossible for a chick to consume. The wetness can also cause illness and cause the chicks to stress, which leads to further health issues.

In other settings the process of microencapsulation is used to deliver substances to animals. The creation of microencapsulated particles is well known for the delivery of substances, such as medications, nutrients and enzymes, to animals and humans alike. Microencapsulation methods include techniques such as spray drying, extrusion, air and electrostatic atomization, and using aerosol atomizers, all within a closed system or reactor where the reaction process can be easily controlled. The reaction process requires a great deal of control, is expensive, and not practical for high throughput applications, such as delivering vaccines and substances to poultry traveling in open containers along a conveyor.

What is needed, therefore, is a high throughput, highly adaptable delivery process that results in semi-firm, non-absorbent gel pieces that are easily and readily consumed by the chicks allowing for better consumption and uniformity of the deliverable substance, thereby resulting in healthier chicks.

BRIEF SUMMARY OF THE INVENTION

The invention is a high throughput process for delivering vaccines, medications, nutrients, such as vitamins, protein, fat, hydration, probiotics, prebiotics and other similar such substances in the form of a semi-firm gel pieces. The gel is non-absorbent, non-smearing, durable and easily consumed by poultry chicks, which results in better uptake and healthier chicks. The semi-firm gel is created by spraying the chicks with a solution containing an alginic acid crosslinking agent and a gel containing alginic acid. The deliverable substance can be added to either the gel or the solution. The deliverable substance, after the chicks are sprayed, may be located on the outside of the gel, within the gel or may move between the inside and outside of the gel due to the semi-firm nature of the resultant gel.

DETAILED DESCRIPTION OF THE INVENTION

The present invention will now be described more fully in detail. This invention should not, however, be construed as limited to the embodiments set forth herein; rather, they are provided so that this disclosure will be complete and will fully convey the scope of the invention to those skilled in the art.

The invention is a process for delivering a substance in the form of consumable semi-firm gel pieces for use with animals, and in particular with poultry chicks. The deliverable substance may be vaccines, medications, nutrients, such as vitamins, protein, fat, hydration, probiotics, prebiotics and other similar such substances. The disclosure discusses the invention in terms of its use with poultry chicks and turkey poults, or simply "chicks", however, it is understood that it is not limited to use with poultry chicks and turkey poults and may be used with any number of other animals.

An apparatus that includes at least one conveyor belt and at least one spray cabinet that is used to spray chicks with various solutions is provided. Particularly, a number of chicks, usually around 100, are placed in an open top container that is placed on the conveyor and transported through one or more spray cabinets. The chicks are commonly processed up to rates of 100,000 chicks/1,000 boxes per hour. The spray cabinets include a plurality of nozzles, which are typically mounted within one or more manifolds, to spray the chicks as they pass through the spray cabinets.

The consumable semi-firm gel, according to the invention, is created by providing a combination of two solutions that are sequentially or simultaneously sprayed onto the chicks. The first solution is a solution containing an alginic acid crosslinking agent, such as the divalent cation $Ca^{2+}$ or a trivalent cation. The solution may be water or a low to high viscosity gel. For example, the first solution may be a mixture of water and powdered calcium, the mixture preferably containing 5% or less of the powdered calcium. The second solution is a gel containing an alginic acid. For example, the second solution may be mixture of a gel and an alginic acid, the mixture preferably containing 5% or less of the alginic acid. The deliverable substance is added to either or both solutions.

Both solutions are applied to the chicks, and crosslinking between the crosslinking agent and the alginic acid creates a semi-firm gel that is firmer than traditional gels and is not absorbable. More specifically, the area of the gel that comes into contact with the first solution initially experiences the crosslinking, which increases the firmness of the gel at that point of contact. For several minutes following the initial contact, the two solutions continue to interact with one another, continuing to increase the firmness of the gel over that period of time. For example, spraying the chicks with the first solution and then applying the gel creates a gel that is firmer on the bottom where it is in contact with the chick. Alternatively, spraying the gel first followed by the first solution creates a gel that is firmer on the top than it is on the bottom. Contact between the chicks, as a result of their preening and moving, increases the rate and amount of crosslinking, creating a gel that is firmer in a relatively short amount of time. Regardless of the sequence of application, the semi-firm gel remains generally as a fully consumable irregular piece on a chick's down and greatly reduces the amount the chicks are wetted in the delivery process. The irregular piece of gel may be in many shapes, including streaks or strings. The semi-firm gel pieces are readily consumed by the chicks, resulting in improved vaccine uptake and healthier chicks.

In one embodiment of the invention, the semi-firm gel is created by applying the two solutions sequentially. In this case, an open-top container is sized to hold approximately 100 chicks relatively closely packed, so that their downs touch one another. The container is placed on a conveyor, which transports the container through a spray cabinet. The spray cabinet includes at least two manifolds, each of which includes a plurality of nozzles, and a plurality of nozzles that are independent of the manifolds. The independent nozzles spray the chicks with the alginic acid crosslinking solution. In this example, the alginic crosslinking solution is preferably sprayed at a rate up to 30 ml per container. The nozzles on the manifolds spray the chicks with the alginic acid gel at rates up to 60 ml per container of chicks. Once applied, the crosslinking solution reacts with the alginic acid gel, forming a semi-firm gel according to the invention, which is then consumed by the chicks. The sprays may be applied in any sequence such that the crosslinking occurs after being applied to the chicks.

In a second embodiment, the two solutions are applied simultaneously. The apparatus is the same as described above.

In a third embodiment, the same process may also be used to create consumable gels that are consumed in, for example, an incubator at a chick hatchery. When the eggs are placed in the incubator, they typically hatch within a 72 hour period although some hatch sooner than others. Within that timeframe, chicks typically have access to hydration and nutrition. Water and food can be messy, and in many cases is incompatible for use in incubators. Nutrition/hydration gels are occasionally provided, however, the conventional gel is only consumable for approximately 24 hours before it evaporates.

In this embodiment, a nutrition/hydration gel containing alginic acid is deposited in a container, such as a food or water trough, located inside incubator and then sprayed with a solution containing the alginic cross-linking agent. As with the semi-firm gel that is created with the first two embodiments, the result is a semi-firm surface on the gel that acts as a layer to protect against evaporation. This allows the gel to remain hydrated and consumable for a longer period of time, typically 72 hours or longer.

It is understood that the embodiments described herein are merely illustrative of the present invention. Variations in the delivery process may be contemplated by one skilled in the art without limiting the intended scope of the invention herein disclosed and as defined by the following claims.

What is claimed is:

1. A process for delivering a semi-firm gel containing a deliverable substance, the process comprising:

a) placing a group of live chicks into a container;

b) spraying the group of live chicks in the container with a first solution containing an alginic acid crosslinking agent; and c) spraying the group of live chicks in the container with a second solution comprising a gel containing alginic acid, wherein the deliverable substance is present in the first solution and/or the second solution, wherein the first solution and the second solution form the semi-firm gel on the group of live chicks in the container, and wherein the semi-firm gel contains the deliverable substance.

2. The process of claim 1, wherein the first solution and the second solution are applied sequentially.

3. The process of claim 1, wherein the first solution and the second solution are applied simultaneously.

4. The process of claim 2, wherein the chicks are sprayed with the first solution and then sprayed with the second solution.

5. The process of claim 2, wherein the chicks are sprayed with the second solution and then sprayed with the first solution.

6. The process of claim 1, wherein the alginic acid crosslinking agent is a divalent cation.

7. The process of claim 1, wherein the alginic acid crosslinking agent is a trivalent cation.

8. The process of claim 1, wherein the alginic acid crosslinking agent is $Ca^{2+}$.

9. The process of claim 1, wherein the second solution contains 5% or less of the alginic acid.

10. The process of claim 1, wherein the second solution is sprayed from a plurality of nozzles on at least two manifolds and the first solution is sprayed from a plurality of nozzles that are independent from the at least two manifolds.

11. The process of claim 10, wherein the second solution is sprayed at a rate of up to 60 ml per container and the first solution is sprayed at a rate of up to 30 ml per container.

* * * * *